United States Patent [19]

Kroener

[11] Patent Number: 4,866,743
[45] Date of Patent: Sep. 12, 1989

[54] COMPUTER TOMOGRAPHY APPARATUS WITH A CLOSED CIRCULATION COOLING SYSTEM

[75] Inventor: Hans-Juergen Kroener, Baiersdorf, Fed. Rep. of Germany

[73] Assignee: Siemens Aktiengesellschaft, Berlin and Munich, Fed. Rep. of Germany

[21] Appl. No.: 182,488

[22] Filed: Apr. 18, 1988

[30] Foreign Application Priority Data

Apr. 29, 1987 [DE] Fed. Rep. of Germany ....... 3714311

[51] Int. Cl.$^4$ ............................................ G01N 23/00
[52] U.S. Cl. ......................................... 378/4; 378/199
[58] Field of Search ............................ 378/4, 199, 200

[56] References Cited

U.S. PATENT DOCUMENTS 4,651,338 3/1987 Hahn .................................... 378/200
4,709,559 12/1987 Dotzauer ............................. 378/200

FOREIGN PATENT DOCUMENTS 0109206 5/1984 European Pat. Off. .
97510 6/1986 Fed. Rep. of Germany .
57-50673 3/1982 Japan .

Primary Examiner—Craig E. Church
Attorney, Agent, or Firm—Hill, Van Santen, Steadman & Simpson

[57] ABSTRACT

A computer tomography apparatus has a stationary part in which a live ring is rotatably seated, the live ring carrying heat generating components such as an x-ray source and a radiation detector, which are disposed on opposite sides of an opening in which an examination subject is received. The stationary part and the live ring limit a sealed annular channel therebetween, the channel having at least one inlet opening and at least one outlet opening for a gaseous coolant. A conduit, which also contains a circulating coolant, has various portions disposed to carry away heat from the heat generating components, and another portion disposed within the annular channel so that the heat can be removed therefrom by the gaseous coolant. The outlet opening and the inlet opening of the channel are connected to form a closed circulation loop for the coolant flowing in the annular channel, with a heat exchanger being disposed between the inlet and the outlet through which the channel coolant, as well as an additional coolant, flow. The closed circulation system avoids air drafts which are undesireable for hygeinic reasons.

13 Claims, 2 Drawing Sheets

4,866,743

COMPUTER TOMOGRAPHY APPARATUS WITH A CLOSED CIRCULATION COOLING SYSTEM

BACKGROUND OF THE INVENTION

1. Field of the Invention

The present invention is directed to a computer tomography apparatus, and in particular to a cooling system for such an apparatus.

2. Description of the Prior Art

Computer tomography devices are known in the art consisting of a stationary apparatus part in which a live ring is rotatably seated, the live ring carrying heat generating components such as an x-ray source and a radiation detector at opposite sides of an opening in which an examination subject is received. For cooling the apparatus, an annular channel is provided which is limited by the stationary apparatus part and the live ring, the channel having at least one inlet and at least one outlet for a gaseous coolant. A conduit, also containing a coolant, is connected to the live ring and has various portions disposed in proximity to the heat generating components so as to carry heat away from those components, and another portion disposed in the annular channel so that the coolant in the channel carries away the heat from the conduit.

Such a computer tomography apparatus is described in published European Application No. 0 182 040, corresponding to U.S. Pat. No. 4,651,338. In this apparatus, the conduit forms a closed cooling circulation loop on the live ring, the heat from the heat generating components, particularly from the x-ray tube, being transferred to the coolant in the conduit. This conduit coolant flows through the portion of the conduit in the annular channel of the live ring, and the heat from the coolant is emitted into the ambient air within the channel, which functions as a gaseous coolant. The air within the channel flows through the channel in a direction from the channel inlet to the channel outlet. Heat elimination from the live ring to the outside of the device is thereby achieved.

A disadvantage of this apparatus, however, is that an air draft, which is undesireable for hygienic reasons, arises in the room in which the tomography apparatus is disposed. In theory, such an air draft could be avoided by supplying the air flowing in the annular channel from the exterior of the room, and eliminating the heat-containing air to the exterior by respective lines connected to the channel inlet and outlet. This would require, however, considerable structural modifications to the room in which the apparatus is disposed, and such lines are additionally undesireable because of the space which they occupy.

SUMMARY OF THE INVENTION

It is an object of the present invention to provide a computer tomography apparatus of the type described above which has a cooling system which avoids the presence of an air draft in the room in which the apparatus is disposed.

The above object is achieved in accordance with the principles of the present invention in a computer tomography apparatus wherein the outlet opening of the annular channel is connected to the inlet opening, thereby forming a closed circulation loop for the coolant which flows in the annular channel. A heat exchanger is also provided between the channel inlet and outlet for removing heat from the channel coolant. This heat exchanger is also supplied with an additional circulating coolant to assist in removal of heat from the channel coolant. Because the coolant in the annular channel flows in a closed circulation loop, air drafts which are present in conventional tomography devices of this type, and which are undesireable for hygienic reasons, cannot occur.

The coolant for the heat exchanger can be either liquid or gas. In the simplest embodiment, the cooling circulation system for the heat exchanger coolant can be opened, and tap water used as the cooling fluid. If this is undesireable, the heat exchanger coolant circulation system may be closed, and another cooling unit may be provided for removing heat from the heat exchanger coolant. This cooling unit may be disposed outside of the room in which the computer tomography apparatus is located. Only a very small portion of the dissipating heat from the components on the live ring is released by radiating into the room in which the apparatus is disposed. This is of particular advantage if the room in which the tomography apparatus is located is climate-controlled, since the air conditioning system for the room is then not significantly additionally loaded by the dissipated heat output of the tomography apparatus.

In another embodiment of the invention, the inlet and outlet opening of the annular channel are disposed in alternating sequence around the circumference of the annular channel, with adjacent inlet and outlet openings being connected to each other. An intensification of the cooling effect is achieved because the coolant flowing through the annular channel is multiply conducted through the heat exchanger, and re-cooled in its path through the annular channel.

Especially efficient heat elimination is achieved in an embodiment wherein the conduit disposed within the annular channel has a plurality of turns, thereby increasing the heat emitting surface of the conduit within the annular channel. The heat emitting surface can be further enlarged by surrounding the outside of the conduit with a wire fabric connected to the conduit in a heat-transmitting fashion. In contrast to other measures, such as ribbing the conduit, the use of the wire fabric has the advantage of barely increasing the flow resistance which the conduit presents to the coolant flowing within the annular channel. In the simplest embodiment, the wire fabric can be formed by a helical wire coil which is helically wound around the conduit and positively connected to the conduit at its points of contact therewith, for example by soldering.

It is also possible to provide a separate exchanger on the live ring which absorbs heat from one or more of the heat generating components, and emits that heat to the coolant which flows through the conduit. The cooling system for the live ring may thus include two closed loop circulation paths and two heat exchangers, namely the aforementioned heat exchanger plus the conduit itself, functioning as a heat exchanger. This embodiment offers the advantage that in the event certain of the heat generating electrical components must be replaced, only the coolant situated in the cooling circulation loop surrounding that particular component must be removed, but the coolant in the conduit need not be removed. The coolant in the live ring circulation systems may be oil, and air is preferable as the coolant in the annular channel.

DESCRIPTION OF THE DRAWINGS

FIG. 3 is a further detail of a portion of the computer tomography apparatus shown in FIG. 1.

DESCRIPTION OF THE PREFERRED EMBODIMENTS

Figure 1:
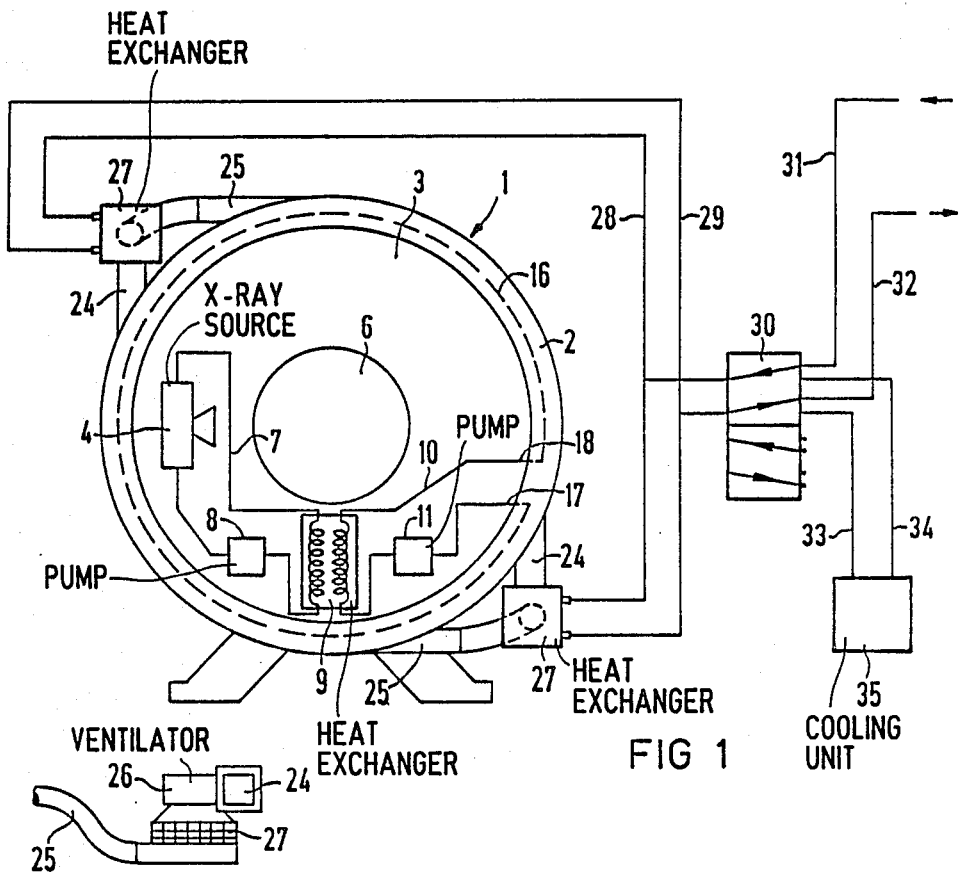
FIG. 1 is schematic diagram of a computer tomography apparatus constructed in accordance with the principles of the present invention.

The basic components of a computer tomography apparatus constructed in accordance with the principles of the present invention are schematically shown in FIG. 1. The apparatus 1 includes a stationary apparatus part 2 on which a live ring 3 is rotatably mounted. The live ring 3 carries an x-ray source 4 and other components (not shown) such as a radiation detector with measuring electronics. For scanning an examination subject disposed in an opening 6, the live ring 3 with the x-ray source 4 and the radiation detector is rotated around the subject, so that the subject is transirradiated from a number of directions. From the respectively received radiation intensities, a computer (not shown) calculates the attenuation values of predetermined points in a slice of the examination subject in a known manner. The resulting image can be visually reproduced on a display or other means (not shown).

For cooling the electrical users (heat generating components) situated on the live ring 3, a closed circulation loop 7 including a pump 8 and a heat exchanger 9 is provided. The coolant for the loop 7 is oil. A second closed cooling circulation loop 10 is also provided, including a pump 11 and sharing the heat exchanger 9. Oil is also used as the coolant in the second loop 10.

Figure 2:
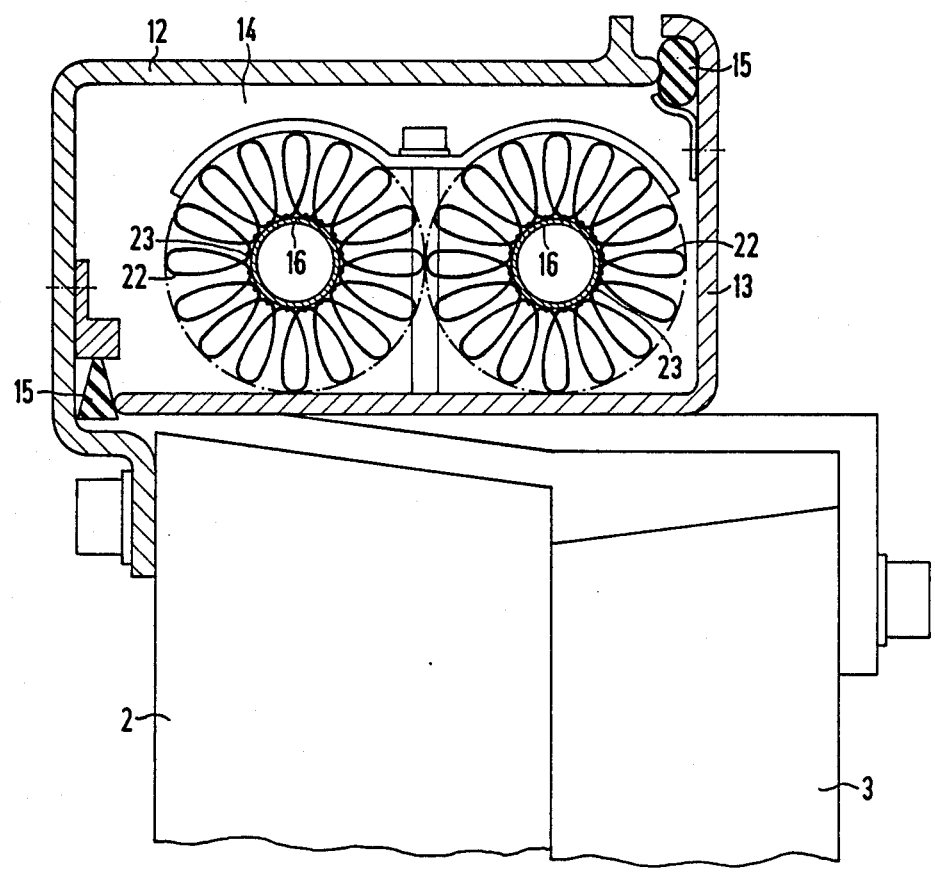
FIG. 2 shows a sectional view through a portion of the apparatus shown in FIG. 1.

As shown in FIG. 2, the stationary apparatus part 2 and the live ring 3 have respective housing portions 12 and 13 attached thereto, which in combination limit or define an annular channel 14. The housing portions 12 and 13 are closed by seals 15 which permit relative rotation of the stationary part 2 and the live ring 3, and the housing portions 12 and 13 respectively connected thereto.

A conduit 16 is disposed within the annular channel 14. The conduit 16 may proceed through a number of turns or loops within the channel 14. In the embodiment shown in FIG. 2, the conduit 16 makes two loops around the live ring 3 and the stationary part 2 within the channel 14. These turns are shown in section in FIG. 2. As seen in FIG. 1, the opposite free ends of the conduit 16 are respectively connected to an inlet 17 and an outlet 18 of the circulation loop 10. The heat arising in the closed housing of the x-ray source 4 is conducted to the heat exchanger 9 by the coolant (oil) flowing through the housing of the x-ray source 4, and is transmitted to the coolant of the loop 10 via the heat exchanger 9. In the annular channel 14, this heat is transmitted to the coolant (such as air) flowing through the annular channel 14.

As also shown in FIG. 2, the conduit 16 has structure for enlarging the surface area thereof, such as a wire fabric 22. The wire fabric 22 is in the form of a helical wire coil which is helically wound around the conduit 16 and connected thereto in heat-transmitting fashion, such as by soldering at points of contact 23. The surface area of the conduit 16 available for heat transfer is thus considerably enlarged.

As can be seen in FIG. 1, the annular channel 14 has two inlet openings 25 and two outlet openings 24 alternatingly arranged on the circumference thereof. Each inlet 24 is connected to the outlet 25 closer thereto, so as to form a closed circulation loop for the cooling air. The cooling air flowing in the annular channel 14, as can be seen in FIG. 3, is conducted through a heat exchanger 27 with a ventilator 26. Each heat exchanger 27 is supplied with a cooling fluid as the coolant therefor, the coolant being admitted via lines 28 and discharged via lines 29. The lines 28 and 29 lead to a valve 30 which permits the lines 28 and 29 to be selectively connected either to an inlet 31 and a discharge 32 for the cooling fluid, for example tap water to form an open cooling circulation path, or to a cooling unit 35 via lines 33 and 34 to form a closed cooling circulation path. The cooling unit 35 may be disposed outside of the room in which the computer tomography apparatus is located.

Heat elimination from the electrical users on the live ring 3 thus ensues via at least three closed cooling circulation paths in the exemplary embodiment. These paths are the cooling circulation loops 7 and 10 and the circulation of the air flowing in the annular channel 14. As a consequence of the air within the channel 14 flowing in a closed circulation path, unwanted air drafts are avoided. The cooling circulation loops 7 and 10 have the advantage that only the coolant situated in the cooling circulation loop 7 in proximity to the heat generating components must be removed upon replacement of one of those components, and the coolant in the circulation loop 10 connected to the conduit 16 does not have to be removed.

Although modifications and changes may be suggested by those skilled in the art it is the intention of the inventor to embody within the patent warranted hereon all changes and modifications as reasonably and properly come within the scope of his contribution to the art.

I claim as my invention:

1. A computer tomography comprising:
    a stationary apparatus part;
    a live ring rotatably stated on said stationary apparatus part, said live ring carrying at least one heat generating component;
    said stationary apparatus part and said live ring in combination limiting sealed annular channel therebetween;
    at least one inlet and at least on outlet for said annular channel on said stationary apparatus part;
    means for circulating a liquid coolant for carrying heat generated by said heat generating component away from said heat generating component, said means for circulating having a portion thereof disposed in said annular channel and preventing exposure of said liquid coolant to said annular channel; and
    means including a heat exchanger connecting said inlet and said outlet of said annular channel in a closed circulation loop for circulating a gaseous coolant in said channel to remove heat from said liquid coolant in said portion of said means for circulating said liquid coolant in said channel.

2. A computer tomography apparatus as claimed in claim 1, further comprising means for circulating a third coolant through said heat exchanger in a closed circulation path including a cooling unit.

3. A computer tomography apparatus as claimed in claim 1, further comprising means for circulating a third coolant through said heat exchanger in an open circulation path.

4. A computer tomography apparatus as claimed in claim 1, having a plurality of inlets and a plurality of outlets, said inlets and said outlets being alternatingly disposed on said stationary apparatus part with each inlet having an outlet closest thereto, and comprising a plurality of additional means each including a heat exchanger connecting each inlet to each outlet closest thereto.

5. A computer tomography apparatus as claimed in claim 1, wherein said means for circulating a liquid coolant is a conduit, and wherein said conduit extends through said annular channel in a plurality of turns.

6. A computer tomography apparatus as claimed in claim 1, wherein said means for circulating a liquid coolant is a conduit, and further comprising means for enlarging the effective exterior surface area available for heat transmission of said conduit.

7. A computer tomography apparatus as claimed in claim 6, wherein said means for enlarging said surface area of said conduit is a wire fabric connected to the exterior of said conduit in heat-conducting fashion.

8. A computer tomography apparatus as claimed in claim 6, wherein said wire fabric is a helical wire coil helically wound around said exterior of said conduit.

9. A computer tomography apparatus as claimed in claim 1, wherein said means for circulating said liquid coolant comprises a first closed loop circulation path having a portion in proximity to said heat generating component, a second closed loop circulation path remote from said heat generating component and including said portion in said annular channel, and means for transferring heat from said first circulation path to said second circulation path.

10. A computer tomography apparatus comprising:
a stationary apparatus part;
a live ring rotatably seated on said stationary apparatus part, said live ring carrying at least one heat generating component;
said stationary apparatus part and said live ring in combination limiting a sealed annular channel therebetween;
at least one inlet and at least one outlet for said annular channel on said stationary apparatus part;
a first closed loop circuit means for circulating a first coolant and disposed in proximity with said heat generating component to remove heat from said heat generating component;
a second closed loop conduit means for circulating a second coolant and disposed remote from said first closed loop conduit means, said second closed loop conduit means having a portion extending through said annular channel;
means for transferring heat from said first closed loop conduit means to said second closed loop conduit means so that said second closed loop conduit means carrier heat away from said closed loop conduit means;
third closed loop means connected to said inlet and outlet of said annular channel for circulating a third coolant through said annular channel to remove heat from said second coolant in said portion of said second closed loop conduit means in said annular channel; and
means for eliminating heat from said third coolant.

11. A computer tomography apparatus as claimed in claim 10, wherein said third coolant is air.

12. A computer tomography apparatus as claimed in claim 10, wherein said third closed loop means for circulating said third coolant includes an inlet and an outlet, and wherein said means for eliminating heat from said third coolant is a heat exchanger connected between said inlet and said outlet of said third closed loop means.

13. A computer tomography apparatus as claimed in claim 10, wherein said third closed loop means for circulating said third coolant includes a plurality of inlets and a plurality of outlets, each inlet having an outlet disposed closest thereto, and wherein said means for eliminating heat from said third coolant is a plurality of heat exchangers respectively connected between each inlet of said third closed loop means and the outlet of said third closed loop means closest thereto.

* * * * *